| United States Patent [19] | [11] Patent Number: 4,840,890 |
| Öhlschläger et al. | [45] Date of Patent: Jun. 20, 1989 |

[54] HARDENED PROTEINIC BINDER LAYER

[75] Inventors: Hans Öhlschläger, Bergisch Gladbach; Karl-Wilhelm Schranz, Odenthal-Hahnenberg; Johannes Sobel, Leverkusen, all of Fed. Rep. of Germany

[73] Assignee: Agfa-Gevaert Aktiengesellschaft, Leverkusen, Fed. Rep. of Germany

[21] Appl. No.: 147,032

[22] Filed: Jan. 19, 1988

Related U.S. Application Data

[63] Continuation of Ser. No. 875,607, Jun. 18, 1986, abandoned.

[30] Foreign Application Priority Data

Jun. 29, 1985 [DE] Fed. Rep. of Germany ....... 3523360

[51] Int. Cl.$^4$ ................................................. G03C 1/30
[52] U.S. Cl. ..................................... 430/622; 430/623; 430/626; 530/354
[58] Field of Search ............... 430/621, 622, 623, 624, 430/625, 626; 530/354

[56] References Cited

U.S. PATENT DOCUMENTS

| 3,490,911 | 1/1970 | Burness et al. ...................... 430/623 |
| 4,298,522 | 11/1981 | Tamura et al. ...................... 526/288 |
| 4,349,624 | 9/1982 | Sobel et al. ........................... 430/622 |
| 4,543,324 | 9/1985 | Himmelmann ...................... 430/622 |
| 4,554,247 | 11/1985 | Yamashita et al. .................. 430/622 |

Primary Examiner—Paul R. Michl
Assistant Examiner—Mark R. Buscher
Attorney, Agent, or Firm—Connolly & Hutz

[57] ABSTRACT

Heteroaromatic vinylsulphone compounds having at least two vinylsulphonyl groups each attached to a carbon atom of a heteroasomatic ring are suitable for hardening proteinic binder layers such as photographic layers containing gelatine as binder.

4 Claims, No Drawings

HARDENED PROTEINIC BINDER LAYER

This application is a continuation of U.S. application Ser. No. 875,607 filed June 18, 1986 for "Hardened Proteinic Binder Layer", now abandoned.

This invention relates to a hardened proteinic binder layer and in particular to a light-sensitive photographic recording material containing at least one silver halide emulsion layer in which the binder layers have been hardened with an aromatic compound containing vinyl sulphonyl groups.

Numerous substances have already been described as hardeners for proteins and in particular for gelatine. These include, for example, metal salts such as chromium, aluminum or zirconium salts, aldehydes and halogenated aldehyde compounds, in particular formaldehyde, dialdehydes and mucochloric acid, 1,2- and 1,4-diketones such as cyclohexane-1,2-diones and quinones as well as chlorides and anhydrides of polybasic organic acids, such as anydrides of tetracarboxylic acids, compounds containing several reactive vinyl groups, such as vinyl sulphones, acrylamides, compounds having at least two heterocyclic, 3-membered rings which are easily split open, such as ethylene oxide and ethylene imine, polyfunctional methane sulphonic acid esters and bis-α-chloracylamido compounds.

High molecular weight hardeners such as polyacrolein and its derivatives or copolymers and alginic acid derivatives have recently become known, particularly for use as hardeners which can harden specific layers selectively.

The use of the above-mentioned compounds for photographic purposes, however, entails numerous serious disadvantages. Some of these compounds are photographically active and therefore unsuitable for hardening photographic recording materials, whereas others have such an adverse effect on the physical properties such as the brittleness of the gelatine layers that they are unstable for this purpose. Others again cause discolouration or a change in the pH during the hardening reaction. Furthermore, for hardening photographic layers it is particularly important that hardening should reach its maximum as soon as possible after the layers have dried in order to ensure, as for example in the case of mucochloric acid or of formaldehyde, that the material to be hardened will not constantly undergo a change in its permeability to the developer solution.

In some cases, cross-linking agents for gelatine have also been found to have a harmful effect on the skin. This applies, for example, to ethyleneimine compounds, which must therefore be excluded on physiological grounds.

It is also known to use trichlorotriazine, hydroxydichlorotriazine and dichloraminotriazines as hardeners. The disadvantages of these hardeners are their relatively high vapour pressure, the release of hydrochloric acid during hardening and the physiological effect of these compounds. Water-soluble derivatives which contain carboxyl and sulphonic acid groups and are obtained by the reaction of cyanuric chloride with 1 mol of a diaminoalkyl or diaminoarylsulphonic acid or carboxylic acid do not show these disadvantages and have therefore recently been proposed as hardeners. Their use in practice, however, is limited as they decompose when left to stand in aqueous solutions owing to their high solubility and therefore rapidly lose their effect.

For hardening photographic layers containing gelatine it is of major importance both from the point of view of the process of preparation and for convenience of processing that the onset of the cross-linking reaction should be determinable within certain limits, for example by suitable choice of the drying temperature or choice of the pH.

Compounds containing two or more acrylamide groups in the molecule, e.g. N,N',N''-tris-acryloyl-hexahydrotriazine or methylene-bis-acrylamide are also known as hardeners for photographic gelatine layers.

Although the hardening effect of these compounds is quite satisfactory after some time, the compounds are only sparingly soluble in water so that hardening may be unevenly distributed in the layer.

Special problems arise with the increasing use of rapid processing of photographic and in particular colour photographic recording materials as such processing makes increased demands on the mechanical properties and swelling properties of the recording material. Added to this are the difficulties arising from the need to use ever thinner photographic layers. It has been attempted to solve such problems by using various types of hardeners. The known hardeners have either given rise to new difficulties or simply prove to be unsuitable. Included among these hardeners are the numerous well-known hardeners containing vinylsulphone groups, one of the longest known of which is divinylsulphone (DE-C 872 153). Divinylsulphone is also unsuitable on account of its toxicity.

Aromatic vinylsulphone compounds have been disclosed in DE-C-1 100 942 and vinylsulphonylalkyl compounds including those containing a heterocyclic ring have been disclosed in DE-A-1 547 733, DE-B2-1 808 685 and DE-A 2 348 194.

The known vinylsulphone compounds have proved to be disadvantageous as hardeners in numerous respects. They are either insufficiently soluble in water and necessitate special measures to enable them to be used in photographic gelatine layers or they have an adverse effect on the drying properties of the layers. Yet other compounds of this kind increase the viscosity of the casting composition, thereby interfering with the formation of layers from the composition. Some of the known vinylsulphone type hardeners also cause migration of photographic additives from one layer to another, especially in colour photographic recording materials, thereby producing colour changes and changes in the photographic properties.

Lastly, DE-A-2 635 518 discloses hardeners consisting of reaction products obtained from the reaction of compounds containing at least three vinylsulphonyl groups in the molecule with compounds containing a water-soluble group and a group capable of reacting with a vinylsulphonyl group. The reaction results in anionic vinylsulphonyl compounds.

These compounds, however, have certain disadvantages. When used in photographic layers containing gelatine, they manifest considerable after-hardening, i.e. their optimum effect is obtained only after the material has been stored for a considerable time. Consequently, swelling of the layer in water diminishes with increasing length of storage and the sensitometric data of the material therefore continuously change. Furthermore, when the known compounds are added to silver halide emulsions containing gelatine, in particular at pH values of around 7, the viscosity rises as the length of digestion time increases so that the emulsions can no longer be smoothly cast.

It is an object of the present invention to provide a hardener for proteinic binders.

It is a further object of the present invention to provide a hardener for photographic hydrophilic binders, in particular gelatine, which will be sufficiently water-soluble for this purpose and have a hardening reaction which rapidly reaches its optimum without any undesirable afterhardening effect.

Accordingly, the present invention relates to a hardened proteinic binder layer and particularly to a light-sensitive photographic recording material comprising at least one layer of binder containing gelatine which has been hardened by means of an aromatic vinylsulphone compound, characterised in that the compound used for hardening the proteinic binder layer or the photographic gelatine-containing layers is a heteroaromatic vinyl sulphone compound having at least two vinylsulphonyl groups each attached to a carbon atom of a heteroaromatic ring.

The hardeners used according to the invention preferably correspond to the following general formula I

Z(—SO₂—CH=CH₂)ₙ    I wherein
Z denotes an optionally substituted heteroaromatic ring containing at least n ring carbon atoms and at least one ring oxygen, ring sulphur or ring nitrogen atom, and
n denotes an integer >2.

The terms "heteroaromatic compounds" and "heteroaromatic rings" are used to denote maximally unsaturated 5-membered or 6-membered rings containing hetero atoms, these rings containing, like benzene, a π-electron sextet (see H.BEYER, Lehrbuch der organischen Chemie, 18th Edition, (1976), page 613). The heteroaromatic ring represented by Z may be, for example, a triazole, thiadiazole, oxadiazole, pyridine, pyrrole, quinoxaline, thiophene, furan, pyrimidine or triazine ring. In addition to the two or more vinylsulphonyl groups, it may carry other substituents and optionally also condensed benzene rings which may in turn be substituted. Substituents such as alkyl, aryl, alkoxy or hydroxyalkyl groups may be useful for modifying the specific properties of the hardener such as the reactivity towards amino groups or solubility in water.

The following are examples of heteroaromatic rings (Z); the bonding lines without a group bonded thereto indicate the position (carbon atoms) to which the vinyl sulphonyl group is bonded:

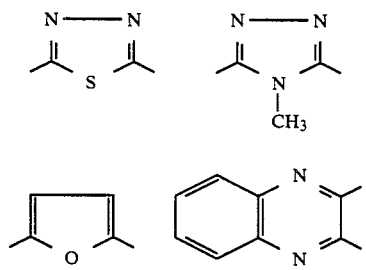

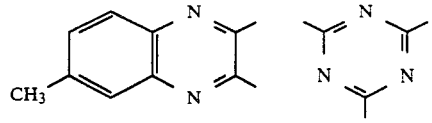

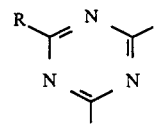

R = Alkyl,
Phenyl,
Alkoxy,

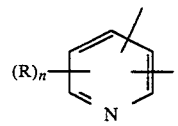

R = Alkyl,
Phenyl,
Alkoxy,
—SO₂—CH=CH₂
n = 0 to 3

The following are examples of hardeners according to the invention:

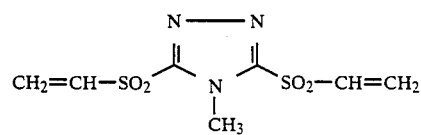  H-1

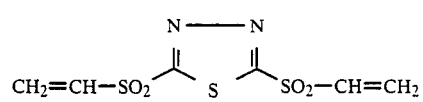  H-2

The hardeners according to the invention corresponding to formula I may be prepared by known methods, e.g. by the reaction of heterocyclic mercapto compounds Z—(SH)ₙ with chloroethanol or the reaction of heterocyclic polyhalogen compounds Z—(Hal)ₙ with mercaptoethanol to form hydroxyethylthio compounds Z—(S—CH₂CH₂—OH)ₙ which may be converted into the hydroxyethylsulphonyl derivatives Z—(SO₂—CH₂—CH₂—OH)ₙ by means of hydrogen peroxide in known manner. When reacted, for example, with thionyl chloride, these hydroxyethylsulphonyl derivatives yield the chloroethylsulphonyl compounds Z—(SO₂—CH₂CH₂—Cl)ₙ from which the hardeners (I) according to the invention are obtained by the removal of hydrogen chloride with bases such as e.g. triethylamine.

The preparation of compound H-1 according to the invention is described in detail below; other compounds may be prepared according to the same scheme.

1ST STAGE 3,5-Bis-(hydroxyethylthio)-4-methyl-1,2,4-triazole 143 g of 3,5-Dimercapto-4-methyl-1,2,4-triazole were introduced into a solution of 130.8 g of KOH in 1000 ml of absolute methanol. The solution was heated under reflux and 188 g of chloroethanol were added dropwise. Stirring was continued at boiling point for a further 4.5 hours and the reaction mixture was then cooled and the precipitated potassium chloride was separated by suction filtration. The methanol was distilled off and the oil residue was stirred up with 700 ml of acetonitrile. The product which separated by crystallisation was suction filtered and dried under vacuum. Yield: 164 g=72%, m.p. 87°–88° C.

2ND STAGE

3,5-Bis-(hydroxyethylsulphonyl)-4-methyl-1,2,4-triazole 8.8 g of Phosphoric acid and 1.3 g of sodium tungstate were added to a solution in 100 ml of water of 101 g of the hydroxyethylthio compound prepared in Stage 1. 166 g of 35% hydrogen peroxide solution were added dropwise while the temperature was maintained at 30° to 35° C. by cooling with ice water. The mixture was stirred for a further 3 hours at room temperature and the substance which crystallised was suction filtered, recrystallised from water and dried under vacuum. Yield: 98 g=76%, m.p. 176°-177° C.

3RD STAGE

3,5-Bis-(chloroethylsulphonyl)-4-methyl-1,2,4-triazole 100 ml of Thionyl chloride are added dropwise to a suspension in 300 ml of toluene of 97.3 g of the hydroxyethylsulphonyl compound obtained in Stage 2 and the mixture is then heated under reflux for 30 minutes and cooled and the precipitated product is suction filtered and recystallised from acetone. Yield: 94.5=85%, m.p. 156° C.

4TH STAGE

3,5-Bis-(vinylsulphonyl)-4-methyl-1,2,4-triazole 79 g of the Chloroethylsulphonyl compound obtained under 3 were suspended in 400 ml of tetrahydrofuran. 61 ml of triethylamine were added dropwise within 30 minutes. The mixture was then stirred for 7 hours at 50° C. and cooled and the triethylamine hydrochloride which crystallised was suction filtered. After the reaction mixture had been concentrated by evaporation under vacuum, the crystalline paste left behind was recrystallised from ethanol with the addition of active charcoal. Yield: 50 g=81%, m.p. 125-126° C.

The reaction of 3,5-dimercapto-1,3,4-thiadiazole with chloroethanol analogously yields the 3,5-bis-(hydroxyethylthio)-1,3,4-thiadiazole, m.p. 80° C. (73%), the oxidation of which with hydrogen peroxide yields 3,5-bis-(hydroxyethylsulphonyl)-1,3,4-thiadiazole, m.p. 110° C. (67%), which in turn may be reacted with thionyl chloride to yield 3,5-bis-(chloroethylsulphonyl)-1,3,4-thiadiazole, m.p. 143° C. (74%) which in turn gives rise to 3,5-bis-(vinylsulphonyl)-1,3,4-thiadiazole, m.p. 97°-99° C. (68%) by elimination of hydrochloric acid with triethylamine.

The compounds of the present invention are capable of rapidly reacting with amino group-containing compounds. Where such amino group-containing compound is a polymer the reaction proceeds with cross-linking of the polymer. Therefore, the compounds of the present invention are valuable hardeners for proteins such as gelatine.

Compared with previous hardeners of the vinylsulphonyl type, the hardeners according to the invention have the advantage of sufficiently hardening photographic layers containing gelatine even when added in smaller quantities.

The compounds to be used according to the invention are generally soluble in water, acetone, methanol or a mixture of waterе and organic solvents. In cases where the solubility in water is low the compound can be used in dispersed form or loaded on a polymer which can be incorporated e.g. in latex form.

The hardeners used according to the invention may be added to the casting solution of a proteinic binder layer such as a photographic layer either some time before casting or immediately before casting, preferably using suitable dosing devices. The compounds may also be added to an overcasting solution which is applied as hardening layer after completed preparation of the photographic recording material. If desired, a complete assembly of layers may be passed through a solution of the hardener, thereby acquiring the necessary quantity of hardener. Lastly, in multilayered arrangements such as colour films and paper, the cross-linking agents according to the invention may be introduced into the whole assembly by means of the intermediate layers.

The hardeners according to the invention are generally employed in a quantity of 0.01 to 15% by weight, preferably 0.1 to 5% by weight, based on dry weight of gelatine in the coating solution. The point in time at which the hardener is added to the coating solution is not critical but the hardener would advantageously be added to silver halide emulsions after chemical ripening.

The hardeners according to the invention may be employed singly or as mixtures of two or more compounds according to the invention or together with other known hardeners. Examples of suitable additional hardeners include formaldehyde, glutaric aldehyde and similar aldehyde compounds, diacetyl, cyclopentadione and similar ketone compounds, bis-(2-chloroethylurea), 2-hydroxy-4,6-dichloro-1,3,5-triazine and other compounds containing reactive halogen as described in U.S. Pat. Nos. 3,288,775, 2,732,303, GB-A-974 723 and GB-A-1 167 207; divinylsulphone, 5-acetyl-1,3-diacryloyl-hexahydro-1,3,5-triazine and other compounds containing a reactive olefine bond as described in U.S. Pat. Nos. 3,635,718, 3,232,763 and GB-A-994 869; N-hydroxymethylphthalimide andother N-methylol compounds as described in U.S. Pat. Nos. 2,732,316 and 2,586,168; isocyanates as described in U.S. Pat. No. 3,103,437; aziridine compounds as described in U.S. Pat. Nos. 3,017,280 and 2,983,611; acid derivatives as described in U.S. Pat. Nos. 2,725,294 and 2,725,295; compounds of the carbodiimide type as described in U.S. Pat. No. 3,100,804; carbamoylpyridinium salts as described in De-A-22 25 230 and DE-A-23 17 677; epoxy compounds as described in U.S. Pat. No. 3,091,537; compounds of the isoxazole type as described in U.S. Pat. Nos. 3,321,313 and 3,543,292; halogenated carboxyaldehydes such as mucochloric acid; dioxane derivatives such as dihydroxydioxane and dichlorodioxane; and inorganic hardeners such as chrome alum and zirconium sulphate. The hardeners according to the invention may be used not only together with the above hardeners but also together with preliminary stages of the compounds described above, such as adducts of alkali metal bisulphites and aldehydes, methylol derivatives of hydantoin and primary fatty nitro alcohols, etc. If hardeners according to the invention are used together with other hardeners, the quantity of hardener according to the invention may be chosen as required according tot he objects to be achieved and the effect produced.

The term "photographic layers" is to be understood in this connection to include layers in general used for photographic recording materials, such as light-sensitive silver halide emulsion layers, protective layers, filterlayers, anti-halation layers, backing layers, image receptor layers or photographic auxiliary layers in general.

Examples of light-sensitive emulsion layers containing gelatine for which the hardeners according to the present invention are particularly suitable include layers containing light-sensitive substances, in particular silver halide, optionally in a spectrally sensitized form. Layers of this kind are normally present in photographic recording materials for a wide variety of black and white or colour photographic processes such as negative, positive, diffusion transfer or printing processes. The hardeners according to the invention have proved to be particularly suitable for hardening photographic combinations of layers used for carrying out colour photographic processes, e.g. combinations containing colour couplers or other colour providing compounds or combinations designed to be treated with solutions containing colour couplers.

The effect of hardeners according to the invention is not impaired by the usual photographic additives and the hardeners are also inert to photographically active substances such as water-soluble or emulsified, water-insoluble colour components, stabilizers, sensitizers and the like. Moreover, they have no deleterious effect on the light-sensitive silver halide emulsion.

The light-sensitive components in the emulsion layers may be any known silver halide such as silver chloride, silver iodide, silver bromide, silver iodobromide, silver chlorobromide, silver iodochlorobromide or the like. The emulsions may be chemically sensitized by means of noble metal compounds, e.g. compounds of ruthenium, rhodium, palladium, iridium, platinum, gold and the like such as ammonium or potassium chloropalladate, potassium chloroplatinate or poassium chloroaurate. The emulsions may also contain special sensitizing agents such as sulphur compounds, tin(II) salts, polyamines or polyalkylene oxide compounds and they may be spectrally sensitized with cyanine dyes, merocyanine dyes and hemicyanine dyes.

The emulsion may contain a wide variety of colour providing compounds such as dye releasers or couplers which may be either coloured or colourless, including those couplers which release a photographically active group in the coupling reaction; stabilizers such as mercury compounds, triazole compounds, azaindene compounds, benzothiazolium compounds or zinc compounds; wetting agents such as dihydroxyalkanes; substances which improve the film-forming properties, e.g. the high molecular weight polymers in the form of particles dispersed in water obtained from the emulsion polymerisation of alkyl acrylate or alkyl methacrylate/acrylic acid or methacrylic acid; styrene/-maleic acid copolymers or styrene/maleic acid anhydride semialkyl ester copolymers, coating auxiliaries such as polyethylene glycol lauryl ether and various other photographic additives.

It is noteworthy that when the hardeners according to the invention are used in colour photographic recording materials containing couplers such as magenta couplers of the 5-pyrazolone series, cyan couplers of the naphthol or phenol series and yellow couplers of the open chain keto methylene series, so-called 2-equivalent or 4-equivalent couplers derived from the above mentioned couplers, and so-called masking couplers containing an arylazo group in the active position, they produce no colour change in the photographic recording materials.

EXAMPLE 1

The following layers were applied in succession to a cellulose triacetate layer support coated with an adhesive layer (the quantities given are based on 1 m$^2$):

1. An antihalation layer containing 4 g of gelatine and 0.7 g of colloidal black silver,
2. A red-sensitive layer 6 μm in thickness containing 35 mmol of silver iodobromide (5 mol-% AgI), 4 mmol of a cyan coupler corresponding to the formula

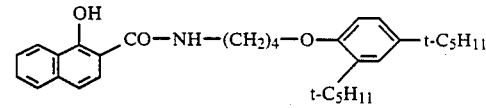

and 6 g of gelatine, 3. a gelatine intermediate layer 0.5 μm in thickness,
4. a green-sensitive layer 6 μm in thickness containing 30 mmol of silver iodobromide (5 mol-% AgI), 1.3 mmol of a magenta coupler corresponding to the formula

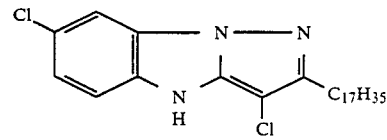

and 5 g of gelatine, 5. a gelatine intermediate layer 0.5 μm in thickness,
6. a yellow filter layer containing 1.5 g of gelatine and 0.2 g of colloidal yellow silver,
7. a blue-sensitive layer 6 μm thickness containing 13 mmol of silver iodobromide (5 mol-% AgI), 2 mmol of a yellow coupler corresponding to the formula

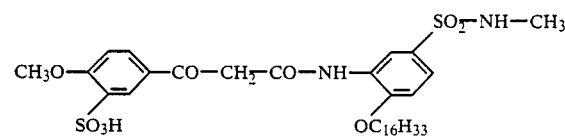

and 5 g of gelatine, and 8. a gelatine layer 1 μm in thickness.

The combination of layers was then dried.

The photographic film thus obtained served as comparison material in the following experiments.

Preparation of the film was repeated but with the addition to the individual layers of each film sample of one of the hardeners according to the invention, H-1 and H-2, or, for comparison, one of the hardeners which were not according to the invention, namely V-1, V-2 and V-3, the hardeners being added in a quantity of 0.6% by weight, based on the quantity of gelatine.

The formulae of the hardeners not according to the invention which were used for comparison are given below:

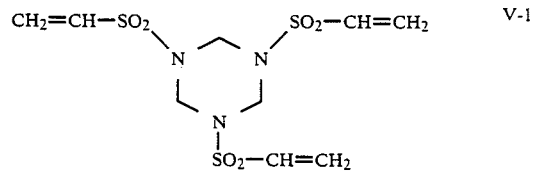

-continued

   V-2

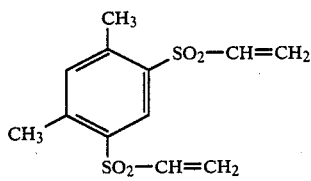   V-3

Samples which had been hardened in the described manner were then tested by the method described below. The results are shown in Table 1.

Hardening of the photographic layers were ascertained from the melting point of the layers, which may be determined as described below.

A combination of layers cast on a support is half dipped in awter which is maintained at 100° C. by continuous heating. The temperature at which the layer runs off the support (formation of streaks) is taken as the melting point or melting off point. When this method of measurement is employed, unhardened protein or colour photographic layers in no case show an increase in melting point. The melting off point under these conditions is in the region of 30° to 35° C.

To determine the water absorption, the test sample was developed as a black sheet by a conventional colour development process and was weighed after the excess water had been stripped off after the final bath. The sample was then dried and reweighed. The difference in the weighings converted from the surface area of the test sample to 1 m² gives the water absorption per m².

Swelling was determined gravimetrically after 10 minutes' treatment of a strip of sample in distilled water at 22° C. It is defined by the swelling factor as follows:

$$\frac{\text{Weight of layer wet}}{\text{Weight of layer dry}} = \text{swelling factor.}$$

To determine the wet scratch resistance, a metal tip of specified size was passed over the wet layer and loaded with a weight of increasing magnitude. The wet scratch strength is that weight at which the tip leaves a visible scratch trace on the layer. A heavy weight corresponds to a high wet scratch strength.

support covered with an adhesive layer. The emulsion layers contained the usual additions of wetting agents, stabilizers, etc:

1. As lowest layer, a 4 μm thick blue-sensitive silver halide emulsion layer containing, per kg of emulsion, 25.4 g of silver chlorobromide (12 mol-% AgCl), 80 g of gelatine and 34 g of the yellow component corresponding to the following formula:

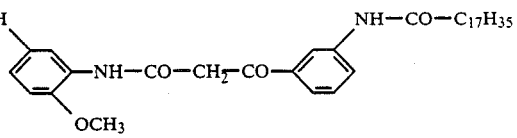

2. as intermediate layer, a 1 μm thick gelatine layer,
3. as middle layer, a 4 μm thick green-sensitive silver halide emulsion layer containing, per kg of emulsion, 22 g of silver chlorobromide (77 mol-% AgCl), 80 g of gelatine and 13 g of magenta component corresponding to the following formula

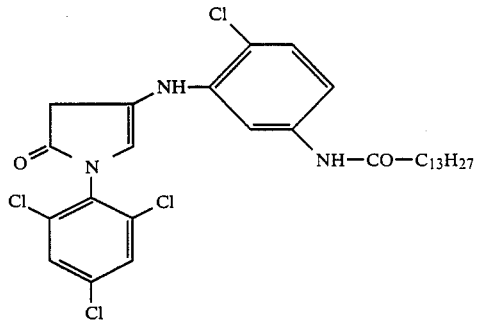

4. a 1 μm thick intermediate layer as described under paragraph 2,
5. as top layer, a 4 μm thick red-sensitive silver halide emulsion layer containing, per kg of emulsion, 23 g of silver chlorobromide (80 mol-% AgCl), 80 g of gelatine and 15.6 g of the cyan component corresponding to the following formula

TABLE 1

| Sample No. | Hardener | Storage 36 h at 57° C., 34% relative humidity | | | Storage 7 days at 36° C., 80% relative humidity | | |
|---|---|---|---|---|---|---|---|
| | | Melting point of layer (°C.) | Swelling factor | Wet scratch strength [N] | Melting point of layer (°C.) | Swelling factor | Wet scratch strength [N] |
| 1 | — | 40 | 6–8 | — | 40 | 6–8 | — |
| 2 | H-1 | 100 | 3.5 | 3.0 | 100 | 3.3 | 5.0 |
| 3 | H-2 | 100 | 3.7 | 2.5 | 100 | 3.5 | 4.5 |
| 4 | V-1 | 45 | 6–7 | <2.0 | 95 | 5 | <2.0 |
| 5 | V-2 | 50 | 5–6 | <2.0 | 100 | 4.5 | <2.5 |
| 6 | V-3 | 34 | 5–6 | <2.0 | 100 | 5 | <3.0 |

No changes in the photographic properties of the samples, such as sensitivity, fogging and gradation, were observed. The swelling values changed only insignificantly in the course of short term and long term storage. The results indicate that the compounds according to the invention have better hardening action, wet scratch strength and layer melting points than the comparison hardeners of the vinylsulphone type.

EXAMPLE 2

A colour photographic material to be viewed by reflected light was prepared by applying the following layers in succession to a polyethylene backed paper

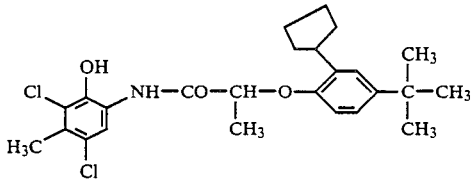

and 6. a 1 μm thick protective layer of gelatine.

When the layer pocket had been dried, aqueous solutions of compounds H-1 and H-2 and of the hardener V-4 which was not according to the invention were applied (in each case 1/200 mol per 100 ml) and the combination of layers when then dried. The layers were tested for cross-linking after they had been stored under normal and tropical atmospheric conditions.

V-4CH₂—(—CH₂—SO₂—CH=CH₂)₂

The results are shown in Table 2.

TABLE 2

| Sample No. | Hardener | Storage 36 h at 57° C., 34% relative humidity | | | Storage 7 days at 36° C., 80% relative humidity | | |
|---|---|---|---|---|---|---|---|
| | | Melting point of layer (°C.) | Swelling factor | Wet scratch strength [N] | Melting point of layer (°C.) | Swelling factor | Wet scratch strength [N] |
| 1 | H-1 | 100 | 3.7 | 2.5 | 100 | 3.4 | 5.5 |
| 2 | H-2 | 100 | 3.9 | 2.3 | 100 | 3.7 | 4.5 |
| 3 | V-4 | 40 | 5–6 | <2.0 | 100 | 3.6 | 5.0 |

It may be seen from Table 2 that the whole combination of layers has been hardened to be fast to boiling by the compounds according to the invention diffusing into it after the layers have only been stored under normal atmospheric conditions (in contrast to Comparison compound V-4 which produces layers fast to boiling only after storage under tropical conditions and gives rise to very severe after-hardening)

When the hardeners according to the invention are used, the intensity of hardening is not found to be reduced according to the distance of the hardener from the uppermost layer (layer in which the hardener is applied).

After the material has been subjected to colour photographic processing in the usual processing baths, the layers obtained have comparable photographic values as regards their sensitivity, fogging and gradation. When used in this form, the hardening system according to the invention is found to be inert towards the emulsion and the colour couplers.

We claim:

1. Layer of a hardened proteinic binder which has been hardened by reacting the amino groups of the protein with a heteroaromatic vinylsulphone compound of the following formula:

Z(—SO₂—CH=CH₂)₂ wherein Z denotes a triazole, thiadiazole, pyridine or triazine which may be substituted further.

2. Hardened binder layer gelatine which has been hardened with 2,5-bis-vinylsulphonyl-2,3,4-thiadiazole or 3,5-bis-vinylsulphonyl-4-methyl-1,2,4-triazole.

3. Light-sensitive photographic recording material comprising at least one gelatin-containing binder layer which has been hardened with a heteroaromatic vinylsulphone compound corresponding to the following formula:

Z(—SO₂—CH=CH₂)₂ wherein Z denotes a triazole, thiadiazole, pyridine or triazine which may be substituted further.

4. Recording material as claimed in claim 3 wherein the binder layer has been hardened with 2,5-bis-vinylsulphonyl-1,3,4-thiadiazole or 3,5-bis-vinylsulphonyl-4-methyl-1,2,4-triazole.

* * * * *